United States Patent [19]

Stanley et al.

[11] Patent Number: 4,461,775

[45] Date of Patent: Jul. 24, 1984

[54] HYDROXYTHIOETHER FATTY ACID DERIVATIVES

[75] Inventors: Kerry G. Stanley, Lansdale; Winston Ho, Hatfield, both of Pa.

[73] Assignee: McNeilab, Inc., Fort Washington, Pa.

[21] Appl. No.: 404,244

[22] Filed: Aug. 2, 1982

[51] Int. Cl.³ ............... C07C 149/20; C07C 149/243; A61K 31/19; A61K 31/22

[52] U.S. Cl. .................... 424/311; 560/153; 560/154; 562/556; 562/581; 424/313; 424/317; 424/319; 260/399; 260/402

[58] Field of Search ............... 424/318, 312, 313, 311, 424/317, 319; 260/402.5, 399; 560/152, 153, 154; 562/581, 556

[56] References Cited

U.S. PATENT DOCUMENTS 3,366,693  1/1968  Randall et al. .................. 568/62

OTHER PUBLICATIONS

Chemical Abstracts, vol. 84, p. 586, Abstract No. 122273w (1976), Gardner et al.
Chemical Abstracts, vol. 87, p. 162, Abstract No. 163021t (1977), Gardner et al.
Chemical Abstracts, vol. 97, p. 58, Abstract No. 33517e (1982), Baker et al.
Tetrahedron Letters, vol. 22, No. 26, pp. 2505–2508 (1981), Baker et al.
Tetrahedron Letters, vol. 22, No. 49, 1981, pp. 4933–4936, Young et al., "The Preparation of Octahydro Leukotrienes C,D, and E Via a Stereoselective Sulfenyllactonization Reaction".

Primary Examiner—Natalie Trousof
Assistant Examiner—Patricia M. Scott
Attorney, Agent, or Firm—David J. Levy

[57] ABSTRACT

Hydroxythioether fatty acid derivatives of formula (I)

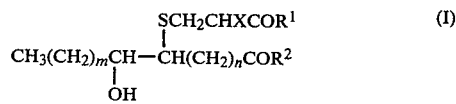

wherein n is 2–5, m is 8–12, $R^1$ is OH, O-loweralkyl, $NH_2$, NH-loweralkyl or NH-carboxyalkyl, $R^2$ is OH or O-lower-alkyl, X is H or $NH_2$ or

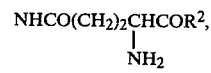

and salts thereof are useful in preventing or alleviating asthma or other allergic diseases.

14 Claims, No Drawings

HYDROXYTHIOETHER FATTY ACID DERIVATIVES

FIELD OF THE INVENTION

This invention relates to novel hydroxythioether fatty acid derivatives, depicted in Formula I below, and to their use as antiallergens, and to pharmaceutical compositions suitable for administration thereof.

BACKGROUND OF THE INVENTION

The chemical structure of SRS-A's (slow reacting substances of anaphylaxis) has been recently reported to be thioaminoacid-containing polyunsaturated fatty acids, namely, 5-hydroxy-6-cysteinylglycinyl-7,9,11,14-eicosatetraenoic acid (leukotriene D, $LTD_4$); 5-hydroxy-6-cysteinyl-7,9,11,14-eicosatetraenoic acid ($LTE_4$); and 5-hydroxy-6-glutathionyl-7,9,11,14-eicosatetraenoic acid ($LTC_4$). These leukotrienes are believed to be the products of arachidonic acid metabolism through the lipoxygenase biosynthetic pathway. Leukotrienes are thought to be potent spasmogens produced or released in allergic diseases. This invention describes compounds, related to the natural leukotrienes, which have been demonstrated to exhibit antiallergic properties and also pharmaceutical compounds and processes for their use as antiallergens.

DESCRIPTION OF THE INVENTION

The present invention relates to novel hydroxythioether fatty acid derivatives having the formula (I)

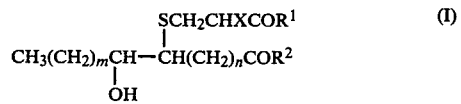

wherein n is an integer from 2 to 5; m is an integer from 8-12; $R^1$ is a member selected from the group consisting of OH, O-loweralkyl, $NH_2$, NH-loweralkyl and NH-carboxyloweralkyl; $R^2$ is OH or O-loweralkyl; X is a member selected from the group consisting of H, $NH_2$,

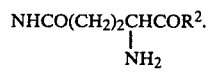

Also compounds of general formula I may have either threo or erythro stereochemical configuration about the two asymmetric carbon atoms.

The therapeutically acceptable salts of the foregoing acids, i.e., when $R^1$ and/or $R^2$ are OH, are also included within the scope of this invention. These basic salts would include, but not be limited to sodium, potassium, calcium, magnesium, triethylamine, tromethamine, dicyclohexylamine and the like. Among the preferred compounds are those wherein both $R^1$ and $R^2$ are hydroxyl.

Also within the scope of this invention are those addition salts from various pharmaceutically acceptable acids for those compounds of this invention where X is nitrogen-containing. These acid salts may include hydrochloride, hydrobromide, phosphate, sulfate, p-toluenesulfonate, malonate, methosulfate and the like.

As used herein "loweralkyl" may be straight or branched chain and have from 1 to 4 carbon atoms, e.g., methyl, ethyl, butyl, isopropyl and the like.

A preferred group of compounds of the present invention are those of formula (I) and salts thereof wherein: n is 3 or 4; m is 10–12, inclusive; $R^1$ is OH or $OCH_3$; $R^2$ is OH or $OCH_3$; and X is H or $NH_2$.

The invention also relates to a process for preventing or alleviating antigen-induced effects by the administration of an animal, especially a mammal, of an antiallergenically sufficient amount of a compound of Formula I, or a pharmaceutically acceptable salt thereof, and to pharmaceutical compositions with a pharmaceutically acceptable carrier.

The compounds of formula (I) may be prepared by the following synthetic procedure. A known olefinic ester of formula (II), wherein n and m, are as previously defined, is transformed by known epoxidation procedures into an oxiranecarboxylic ester of formula (III). This is readily accomplished by treatment of II with an appropriate organic peracid, for example, m-chloroperbenzoic acid, trifluoroperacetic acid, peracetic acid, perphthalic acid and the like in an inert aprotic organic solvent, such as, an aromatic hydrocarbon, a halogenated hydrocarbon

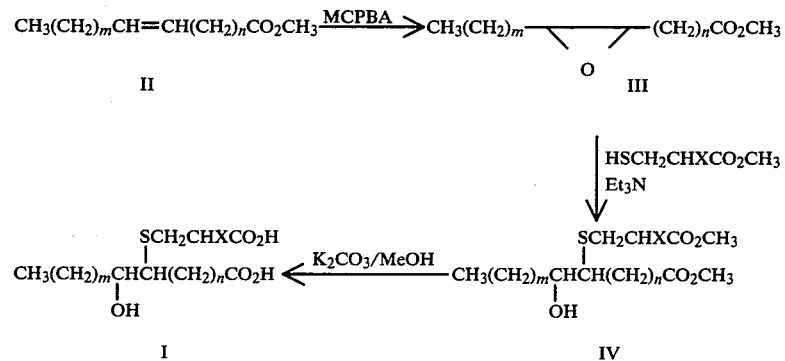

and the like, under reflux condition.

The hydroxy thio compound of formula (IV) may be obtained by opening of the epoxide ring of formula (III) with an appropriate thio compound in the presence of a base, preferably triethylamine, in refluxing methanol.

The choice of the appropriate olefin will determine the relative stereochemistry of the final products. That is, a cis olefin on epoxidation yields a cis epoxide, as is well documented in the literature, which in turn on ring opening with the appropriate thio compound gives compounds of formula IV, with threo stereochemistry. In an analogous manner, the choice of a trans olefin leads to compounds of formula IV with erythro stereochemistry.

Conventional hydrolysis of the hydroxy thio ester of formula IV is then utilized to yield the corresponding diacids of formula (I). Preferably, typical alkaline ester-to-acid hydrolysis conditions are employed, for example, $K_2CO_3$ in aqueous methanol at reflux temperature.

The utility of the compounds described herein as antiallergy agents is demonstrated by the following in vitro isolated tissue screens.

ISOLATED TISSUE (a) guinea pig ileum: This test demonstrates the effectiveness of an agent in preventing the contraction of gunea pig ileum caused by SRS-A. Male guinea pigs are sacrificed, the ileum removed, washed and cut into 1–1.5 cm segments and placed in oxygenated Krebs Henslert solution in a tissue bath under 500 mg tension. The tissue is exposed to 5 mg/ml histamine at 1–3 minute intervals until a reproducible response is obtained. Atropine ($1 \times 10^{-5}$M) and chlorpheniramine ($1 \times 10^{-5}$M) are added followed by 1–2 biological units of SRS-A. After washing the tissue, the response to $BaCl_2$ ($1 \times 10^{-3}$M) was also noted. Thirty minutes hence atropine, chlorpheniramine and test drug are added to the tissue bath followd five minutes later by the same concentration of SRS-A. After washing, the tissue is again challenged with SRS-A. The tissue is also challenged with $BaCl_2$ ($1 \times 10^{-3}$M) in the presence of test drug. A test compound is considered active if it demonstrates a 50% reduction in contraction of guinea pig ileum strip due to SRS-A at a maximum concentration of $10^{-4}$M; $IC_{50} < 100$ μm.

(b) guinea pig parenchymal strip: This test demonstrates the effectiveness of an agent in preventing the contraction of guinea pig parenchymal tissue by immunological release of SRS-A. Male guinea pigs were sensitized by direct administration (i.p.) of egg albumin (1 mg) and *Bordetella pertussis* two weeks prior to the experiment. The guinea pigs were sacrificed and lungs removed. Strips of subpleural parenchyma were prepared from the left and right diaphragmatic lobes and suspended in a tissue bath under 1 g of tension. After a one hour equilibration period, a dose response to histamine ($10^{-7}$ to $10^{-4}$M) induced contractions was performed to determine maximal contraction. The tissues were then washed and allowed to relax to baseline. Chlorpheniramine ($10^{-4}$M), indomethacin ($10^{-5}$M) and test compound were added 30 minutes prior to challenge with egg albumin. The response to antigen was measured in milligrams of tension. A test compound is considered active if it demonstrates a 50% reduction in contraction of a guinea pig parenchymal strip, relative to a control tissue (taken from the same animal), with an $IC_{50} \leq 100$ μm.

A significant inhibition of the contraction of isolated tissue produced either by challenge with SRS-A or by immunological release of SRS-A from that of controls is observed with the test compounds.

The results of these tests, employing the administration of various illustrative compounds of the present invention are shown in Table I.

TABLE I

EFFECT OF TEST COMPOUNDS ON SRS—A INDUCED CONTRACTIONS OF ISOLATED TISSUE $$CH_3(CH_2)_{10}-\underset{\underset{OH}{|}}{CH}-\underset{\underset{SCH_2CH-COR^1}{\overset{X}{|}}}{CH(CH_2)_4COR^2}$$

| | X | $R^1$ | $R^2$ | Isomer | G.P. Ileum $IC_{50}$, μm | Parenchymal Strip $IC_{50}$, μm |
|---|---|---|---|---|---|---|
| 1 | H | $OCH_3$ | $OCH_3$ | threo | 1.0 | >100 |
| 2 | H | OH | OH | threo | 0.24 | 80 |
| 3 | $NH_2$ | $OCH_3$ | $OCH_3$ | threo | 1.3 | >100 |
| 4 | H | $OCH_3$ | $OCH_3$ | erythro | — | 10 |

The above test results show the usefulness of the compounds of this invention in the treatment of allergic diseases and most specifically in the treatment of asthma.

The compounds of the present invention are useful for treating allergic diseases by administering to subjects in need of treatment an effective symptomatic reducing dose of a compound of formula I or its pharmaceutically-acceptable salt as the active agent. The active agents may or may not be administered as an admixture with a pharmaceutically-acceptable carrier.

The operable ranges for carrying out the treatment is the administration orally or parentally, of from 1 to 1250 mg of said compound of formula I. Operable amounts are generally in the range of 1 to 100 mg/kg per day of body weight.

The following examples will exemplify various preferred embodiments of the present invention, but are not to be construed as limiting.

EXAMPLE 1

Threo Methyl 7-Hydroxy-6{[2-(methoxycarbonyl)ethyl]thio}octadecanoate

To a solution of 5.44 g (0.017 mole) of methyl 6,7-cis-epoxyoctadecanoate (Steger and Van Loon, Rec. Trav. Chim., Bays-Pas., 46, 702 (1927)) in 10 ml of absolute MeOH, at room temperature under an atmosphere of argon, was added 9.67 ml (0.070 mole) of $Et_3N$ and 8.35 g (7.7 ml, 0.070 mole) of methyl 3-mercaptopropionate. The reaction mixture was heated to reflux for 18 hours, cooled, diluted with 100 ml of water, and extracted into ether. The organic extracts were washed with 1N HCl, followed by water, and dried over $MgSO_4$, filtered and evaporated in vacuo to give 10 g of crude product. This crude product contains an equal amount of the desired compound and the regioisomeric compound; threo methyl 6-hydroxy-7{[2-(methoxycarbonyl)ethyl]thio}octadecanoate. Purification via Waters Prep 500 LC gave 1.47 g (20%) of pure desired compound as a gold oil: i.r. ($CHCl_3$) 1733, 1440, 1363 and 1231 cm$^{-1}$; nmr ($CDCl_3$) δ(TMS) 3.70 (3, S, $CO_2CH_3$), 3.67 (3, S, $CO_2CH_3$), 3.50 (1, M), 2.25–2.91 (8, M, 1-exchangeable), 1.25–1.75 (26, broad M) and 0.88 ppm (3, t, $CH_3$—); mass spectrum (70 e/v) 417 (M-15), 401, 295, 263, 248, 161.

Anal. Calcd. for $C_{23}H_{44}O_5S$: C, 63.85; H, 10.25; S, 7.41. Found: C, 64.08; H, 9.84; S, 7.42.

EXAMPLE 2

Threo 6-(2-Carboxyethyl)thio-7-hydroxyoctadecanoic Acid

A solution of 1.45 g (0.0034 mole) of threo methyl 7-hydroxy-6{[2-(methoxycarbonyl)ethyl]thio}octadecanoate (Example 1) in 85 ml of 5:1 MeOH/H$_2$O (v/v) was treated with 4.63 g (0.034 mole) of K$_2$CO$_3$ and heated to reflux for 2 hours. The reaction mixture was cooled, diluted with 100 ml of water and acidified to pH=2.0 with 6N HCl. The aqueous mixture was extracted with ether (3×100 ml) and the organic extracts dried over MgSO$_4$, filtered and evaporated in vacuo to give 1.10 g (80%) of pure diacid as a hemihydrate: i.r. (CHCl$_3$) 2900–3300 (broad), 1714, 1413, 1238 (cm$^{-1}$); nmr (CDCl$_3$) δ(TMS) 7.75 (3, broad, OH, CO$_2$H, exchangeable), 3.50 (1, broad M), 2.20–3.00 (7, broad M), 1.25–1.80 (26, broad M) and 0.90 ppm (3, t, CH$_3$—).

Anal. Calcd. for C$_{21}$H$_{40}$O$_5$S.½H$_2$O: C, 60.98; H, 9.99; S, 7.75. Found: C, 61.14; H, 9.97; S, 7.73.

EXAMPLE 3

Threo S-(6-Hydroxy-1-methoxycarbonyl-5-heptadecyl)-L-cysteine Methyl Ester

To a solution of 12.0 g (0.039 mole) of methyl 6,7-cis-epoxyoctadecanoate (Steger and Van Loon, Rec. Trav. Chim., Bays-Pas., 46, 702 (1927)) in 150 ml of absolute MeOH was added 14.4 g (0.107 mole) of methyl L-cysteinate (freshly prepared from its HCl salt) and 21.4 ml (0.154 mole) of Et$_3$N and this reaction mixture heated to reflux for 16 hours. The reaction mixture was cooled, diluted with 250 ml of water and extracted into ether (3×200 ml). The organic extracts were dried over MgSO$_4$, filtered and evaporated in vacuo to give 17 g of crude product. Purification to give a mixture of the two regioisomeric products was accomplished via two pases on a Waters Prep 500 LC. The first pass utilized a 2:1 EtOAc/Hex elluent and on the second pass a 60:1 CHCl$_3$/MeOH elluent. This purification gave 6.1 g (35%) of product as a gold oil. Separation of the regioisomeric products was accomplished through repetitive column chromatography: i.r. (CHCl$_3$) 3389, 1740, 1440, 1236 and 1175 cm$^{-1}$; nmr (CDCl$_3$) δ(TMS) 3.72 (3, S, CO$_2$CH$_3$), 3.65 (3, S, CO$_2$CH$_3$), 3.60 (1, M, —CH—CO$_2$CH$_3$), 3.45 (1, M), 2.88 (2, AB multiplet J=2 H$_z$, 4 H$_z$), 2.37 (6, M, 3-exchangeable), 2.25–2.80 (26, M) and 0.88 ppm (3, t, —CH$_3$); mass spectrum (70 e/v) m/e 447, 429, 295, 263:

Anal. Calcd. for C$_{23}$H$_{45}$NO$_5$S: C, 61.71; H, 10.13; N, 3.13; S, 7.16. Found: C, 61.88; H, 9.98; N, 3.60; S, 7.19.

EXAMPLE 4

Erythro Methyl 7-Hydroxy-6-{[2-(methoxycarbonyl)ethyl]-thio}octadecanoate

The method of Example 1 was applied to 10.0 g (0.032 mole) of methyl 6,7-trans-epoxyoctadecanoate to give 28.0 g of crude product. This crude product contains an equal amount of desired compound and the regioisomeric compound; erythro methyl 6-hydroxy-7{[2-(methoxycarbonyl)ethyl]thio}octadecanoate. Purification via Waters Prep 500 LC gave 1.59 of pure desired compound as an oil: ir (CHCl$_3$) 1736, 1441, 1364 and 1227 cm$^{-1}$; nmr (CDCl$_3$) δ(TMS) 3.69 (3, s, CO$_2$CH$_3$), 3.67 (1, m), 3.65 (3, s, CO$_2$CH$_3$), 2.30–2.90 (8, m, 1-exchangeable), 1.25–1.80 (26, broad m) and 0.90 ppm (3, t, CH$_3$).

Anal. Calcd for C$_{23}$H$_{44}$O$_5$S: C, 63.85; H, 10.25; S, 7.41. Found: C, 63.74; H, 10.29; S, 7.39.

The following examples illustrate the preparation of various pharmaceutical compositions of the present invention:

EXAMPLE 5

1,000 hard gelatin capsules, each containing 200 milligrams of active ingredient, which is threo methyl 7-hydroxy-6{[2-(methoxycarbonyl)ethyl]thio}octadecanoate or alternatively the compound of any previous example in free acid, base or salt form are prepared from the following formulation:

|  | Grams |
| --- | --- |
| Active ingredient | 200 |
| Starch | 100 |
| lactose | 150 |
| Talc | 50 |
| Calcium stearate | 5 |

A uniform mixture of the ingredients is prepared by blending and employed to fill two-piece hard gelatin capsules. The capsules are suitable to be orally administered to subjects with allergic diseases, such as asthma.

EXAMPLE 6

Gelatin capsules are prepared as described in Example 5, except that in the formulation, 400 grams of threo 6-(2-carboxyethyl)thio-7-hydroxyoctadecanoic acid is employed as active agent providing capsules containing 400 milligrams of said active agent.

EXAMPLE 7

1,000 compressed tablets, each containing 500 milligrams of threo S-(6-hydroxy-1-methoxycarbonyl-5-heptadecyl)-L-cysteine methyl ester as the active ingredient are prepared from the following formulation:

|  | Grams |
| --- | --- |
| Active ingredient | 500 |
| Starch | 75 |
| Microcrystalline cellulose | 100 |
| Calcium stearate | 5 |

The finely powdered ingredients are mixed well an granulated with 10 percent starch paste. The granulation is dried and compressed into tablets using starch as a disintegrant and calcium stearate as a lubricant.

EXAMPLE 8

Parenteral formulations, for administration, i.v. or i.p. are prepared as follows:

|  | Quantity |
| --- | --- |
| Active ingredient | 40 mg |
| Benzyl alcohol | 9 mg |
| Hydrochloric acid, q.s. | * |
| Water for injection, q.s. | 1 ml |

*to pH = 3–5

We claim:

1. A hydroxythioether fatty acid derivative represented by the following formula (I) and which may be of either the threo or erythro configuration:

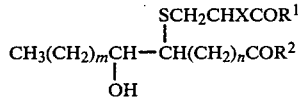

wherein n is an integer from 2 to 5; m is an integer from 8–10; $R^1$ is a member selected from the group consisting of OH, O-loweralkyl, $NH_2$, NH-loweralkyl and NH-carboxyloweralkyl and $R^2$ is OH, or O-loweralkyl; X is a member selected from the group consisting of H, $NH_2$ and

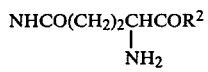

and the therapeutically acceptable basic salts thereof when $R^1$ or $R^2$, or both, are OH; and the therapeutically acceptable acid addition salts thereof where X is $NH_2$ or

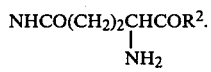

2. A derivative of claim 1 wherein in said formula (I)
n is 3–4
m is 10
$R^1$ is OH or $OCH_3$
$R^2$ is OH or $OCH_3$ and
X is H or $NH_2$.

3. A derivative of claim 1 which is threo methyl 7-hydroxy-6-([2-methoxycarbonyl)ethyl]thio)octadecanoate.

4. A derivative of claim 1, which is threo 6-(2-carboxyethyl)thio-7-hydroxyoctadecanoic acid.

5. A derivative of claim 1, which is threo S-(6-hydroxy-1-methoxycarbonyl-5-heptadecyl)-L-cysteine methyl ester.

6. A derivative of claim 1, which is erythro methyl 7-hydroxy-6-([2-(methoxycarbonyl)ethyl]thio)octadecanoate.

7. A method for treating allergic diseases by administering to an animal having such a disease, a therapeutically effective amount of a hydroxythioether fatty acid derivative represented by the following formula (I) and which may be of either the threo or erythro configuration:

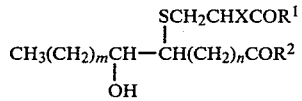

wherein n is an integer from 2 to 5; m is an integer from 8–12; $R^1$ is a member selected from the group consisting of OH, O-loweralkyl, $NH_2$, NH-loweralkyl and NH-carboxyloweralkyl; and $R^2$ is OH, or O-loweralkyl; X is a member selected from the group consisting of H, $NH_2$ and

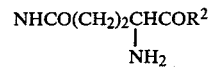

and the therapeutically acceptable basic salts thereof when $R^1$ or $R^2$, or both, are OH; and the therapeutically acceptable acid addition salts thereof where X is $NH_2$ or

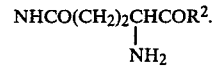

8. A method according to claim 7 which comprises administering to said animal from about 1 to 1250 milligrams per unit dose of said derivative of formula (I).

9. A method according to claim 7 wherein the derivative administered is selected from the group consisting of threo methyl 7-hydroxy-6-([2-(methoxycarbonyl)ethyl]thio)octadecanoate; threo 6-(2-carboxyethyl)thio-7-hydroxyoctadecanoic acid; threo S-(6-hydroxy-1-methoxycarbonyl-5-heptadecyl)-L-cysteine methyl ester; and erythro methyl 7-hydroxy-6-([2-(methoxycarbonyl)ethyl]thio)octadecanoate.

10. A method for the treatment of asthma or other allergic diseases in mammals which comprises the administering thereto between 1 and 100 mg/kg per day of a hydroxythioether fatty acid derivative represented by the following formula (I) and which may be of either the threo or erythro configuration:

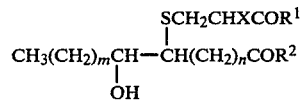

wherein n is an integer from 2 to 5; m is an integer from 8–12; $R^1$ is a member selected from the group consisting of OH, O-loweralkyl, $NH_2$, NH-loweralkyl and NH-carboxyloweralkyl; and $R^2$ is OH, or O-loweralkyl; X is a member selected from the group consisting of H, $NH_2$ and

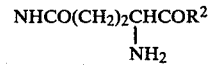

and the therapeutically acceptable basic salts thereof when $R^1$ or $R^2$, or both, are OH; and the therapeutically acceptable acid addition salts thereof where X is $NH_2$ or

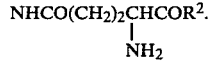

11. A method according to claim 10 wherein the derivative administered is selected from the group consisting of threo methyl 7-hydroxy-6-([2-methoxycarbonyl)ethyl]thio)octadecanoate; threo 6-(2-carboxyethyl)thio-7-hydroxyoctadecanoic acid; threo S-(6-hydroxy-1-methoxycarbonyl-5-heptadecyl)-L-cysteine methyl ester; and erythro methyl 7-hydroxy-6-([2-methoxycarbonyl)ethyl]thio)octadecanoate.

12. A pharmaceutical composition suitable for administration in treating allergic diseases in dosage unit form comprising an antiallergenically effective amount of a derivative of claim 1 in admixture with a pharmaceutically acceptable carrier.

13. A pharmaceutical composition according to claim 12 wherein the pharmaceutically acceptable carrier is either one suitable for oral use or one suitable for parenteral use.

14. A composition according to claim 13, wherein the particular derivative used therein is selected from the group consisting of threo methyl 7-hydroxy-6([2-(methoxycarbonyl)ethyl]thio)octadecanoate; threo 6-(2-carboxyethyl)thio-7-hydroxyoctadecanoic acid; threo S-(6-hydroxy-1-methoxycarbonyl-5-heptadecyl)-L-cysteine methyl ester; and erythro methyl 7-hydroxy-6([2-methoxycarbonyl)ethyl]thio)octadecanoate.

* * * * *